(12) United States Patent
Kroll et al.

(10) Patent No.: US 6,754,531 B1
(45) Date of Patent: Jun. 22, 2004

(54) ANTI-TACHYCARDIA PACING METHODS AND DEVICES

(75) Inventors: Mark Kroll, Simi Valley, CA (US); Eric S. Fain, Menlo Park, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 255 days.

(21) Appl. No.: 10/045,570

(22) Filed: Oct. 19, 2001

(51) Int. Cl.[7] .................................................. A61N 1/36
(52) U.S. Cl. .............................................. 607/14; 607/9
(58) Field of Search .......................... 607/14, 9, 4, 5

(56) References Cited

U.S. PATENT DOCUMENTS

| | | | |
|---|---|---|---|
| RE27,652 E | * 5/1973 | Mirowski | 607/6 |
| 4,088,140 A | 5/1978 | Rockland et al. | 128/419 PG |
| 4,181,133 A | 1/1980 | Kolenik et al. | 128/419 PG |
| 4,280,507 A | 7/1981 | Rosenberg | 128/696 |
| 4,390,021 A | 6/1983 | Spurrell et al. | 128/419 PG |
| 4,398,536 A | 8/1983 | Nappholz et al. | 128/419 PG |
| 4,408,606 A | 10/1983 | Spurrell et al. | 128/419 PG |
| 4,488,553 A | 12/1984 | Nappholz et al. | 128/419 PG |
| 4,488,554 A | 12/1984 | Nappholz et al. | 128/419 PG |
| 4,958,632 A | 9/1990 | Duggan | 128/419 PG |
| 5,243,978 A | 9/1993 | Duffin, Jr. | 607/11 |
| 5,325,870 A | 7/1994 | Kroll et al. | 607/122 |
| 5,330,509 A | 7/1994 | Kroll et al. | 607/14 |
| 5,336,253 A | 8/1994 | Gordon et al. | 607/122 |
| 5,543,183 A | 8/1996 | Streckert et al. | 607/5 |
| 5,800,465 A | * 9/1998 | Thompson et al. | 607/9 |
| 5,902,324 A | 5/1999 | Thompson et al. | 607/9 |
| 5,978,705 A | 11/1999 | KenKnight et al. | 607/5 |
| 5,995,871 A | 11/1999 | Knisley | 607/15 |
| 6,266,563 B1 | 7/2001 | KenKnight et al. | 607/5 |
| 2003/0120315 A1 | 6/2003 | Spinelli et al. | 607/14 |

OTHER PUBLICATIONS

Bocchiardo, et al.; "Efficacy of Biventricular Sensing and Treatment of Ventricular Arrhythmias"; Pace, vol. 23; Nov. 2000, Part II; pp. 1989–1991.

Kroll, et al.; "Implantable Cardioverter Defibrillator Therapy: The Engineering–Clinical Interface"; copyright 1996, second printing 1997; Chapter 16, Anti–Tachycardia Pacing and Cariodoversion; pp. 325–342.

* cited by examiner

Primary Examiner—Angela D. Sykes
Assistant Examiner—Roderick Bradford
(74) Attorney, Agent, or Firm—Steven M. Mitchell

(57) ABSTRACT

An improved method and device for performing anti-tachycardia pacing (ATP) to convert a ventricular tachycardia (VT) to normal sinus rhythm. Pairs of pacing/sensing electrodes are placed in or on each of the left and right ventricles. Each pair of electrodes is shorted together to produce unipolar electrodes that are used for ATP.

13 Claims, 9 Drawing Sheets

ANTI-TACHYCARDIA PACING METHODS AND DEVICES

This application is related to copending application Ser. Nos. 10/045,495, 10/039,734, 10/067,116 and 10/045,494 all filed on Oct. 19, 2001.

FIELD OF THE INVENTION

The present invention relates generally to implantable cardiac stimulation devices. The present invention more particularly relates to methods and devices for multi-chamber anti-tachycardia pacing.

BACKGROUND OF THE INVENTION

The heart is a series of pumps that are carefully controlled by a very special electrical system. This electrical system attempts to regulate the heart rate between 60 and 100 beats per minute. The initial electrical signal originates near the top of the upper chamber on the right side of the heart.

This chamber is called the "right atrium" and the special tissue that generates the signal is called the "sino-atrial" or SA node.

The electrical signal continues in a downward fashion through the "atrio-ventricular" or AV node, where the signal is slowed slightly by special tissue. The AV node is the "doorway" or relay station to the bundle of His (pronounced Hiss), and the bundle branches in the lower chambers of the heart.

After passing through the left and right bundle branches, the impulse arrives at the Purkinje fibers, where it is transmitted to the muscle cells of the left and right ventricles. Because of the specialized way in which the impulse is transmitted, the ventricles contract almost simultaneously.

With normal conduction, the cardiac contractions are very organized and timed so that the top chambers (the atria) contract before the lower chambers and the heart rate is maintained between 60 and 100 beats per minute.

Abnormally fast heart rates are called tachycardias. As used herein, the term tachycardia means a heartbeat at a rate which is abnormally high and accordingly considered to be dangerous if permitted to continue, or any arrhythmia involving recognizable heartbeat patterns containing repetitions which are in excess of a periodic heartbeat within a safe range.

When the ventricular chambers beat too quickly, the arrhythmia (i.e., unusual heart rhythm) is known as ventricular tachycardia. When ventricular tachycardia (VT) occurs, the ventricles may not be able to fill with enough blood to supply the body with the oxygen rich blood that it needs. Symptoms of VT include feeling faint, sometimes passing out, dizzyness, or a pounding in the chest.

Ventricular tachycardia may be controlled by medication in some cases. If medications are not effective, the physician may elect to control the rhythm by electrical methods. The most common electrical therapy for VT is implantation of a device known as an Implantable Cardioverter Defibrillator (ICD). The ICD applies an electric shock to the heart muscle to interrupt or disrupt the fast rhythm. The electric shock may be in the form of specially timed pacemaker pulses (unfelt by the patient) or by high voltage shock. The high voltage shock, if required, is usually painful to the patient. Accordingly, it is preferential to use pacemaker pulses (also referred to as pacing pulses).

Tachycardias can result due to any number of reasons. For example, patients who have had myocardial infarctions, or other diseases that create scarring in the ventricular region of the heart, often develop monomorphic ventricular tachycardias. A monomorphic ventricular tachycardia (MVT) is a type of tachycardia that originates from one ventricular focus. These tachycardias often arise in and around the area of scarring on the heart. They are typically uniform and typically occur at a regular rate. Faster MVTs are often associated with hemodynamic compromise, whereas slower MVTs can be very stable.

Anti-Tachycardia Pacing (ATP) has been used to convert ventricular tachycardias into normal sinus rhythm. However, conventional ATP has not proved to be one hundred percent successful at returning the heart to normal sinus rhythm. Additionally, in a rare case, conventional ATP will accelerate the rhythm to ventricular fibrillation. Accordingly, improved methods and apparatuses for decreasing the failure rate of ATP are required. Some of the prior patent documents which teach ATP using low voltage shock therapy systems include U.S. Pat. Nos. 4,408,606, 4,398,536, 4,488,553, 4,488,554, 4,390,021, 4,181,133 and 4,280,502.

Tachycardia is often the result of electrical feedback within the heart; a natural beat results in the feedback of an electrical stimulus which prematurely triggers another beat. By interposing a stimulated heartbeat (i.e., a pacing pulse), the stability of the feedback loop is disrupted. For example, patients with MVT can often times be successfully paced out of the tachycardia using a rapid burst of high rate pacing. The burst consists of a selected number of pulses all delivered at the same rate, an accelerating rate, or an alternating accelerating/decelerating rate. The mechanism that determines success of the burst is the ability to peel-back the refractories between the pacing site and the origin of the arrhythmia and penetrate the reentrant loop.

In conventional ATP, anti-tachycardia pacing pulses are delivered using two electrodes within the right ventricle (RV). The inventors of the present invention are aware of one study of the efficacy of bi-ventricular (BV) ATP. See Bocchiardo et al., "Efficacy of Biventricular Sensing and Treatment of Ventricular Arryhthmias," PACE, Vol. 23, November 2000, pp. 1989–1991. In the Bocchiardo study, the BV pacing was accomplished using an RV tip electrode, an RV proximal electrode, and an LV tip electrode. The Bocchiardo study concluded that "[t]he success rates of spontaneous VT termination by BV ATP versus RV ATP were comparable." The inventors of the present invention, however, believe that there may be many advantages to BV ATP.

There is a need for improved methods and devices for ATP. More specifically, there is a need to increase the success rate (i.e., decrease the failure rate) of VT termination using ATP. Such improved methods and devices will preferably also reduce the amount of time required to convert a tachycardia to normal sinus rhythm.

BRIEF SUMMARY OF THE INVENTION

The present invention relates to improved methods and devices for performing anti-tachycardia pacing (ATP) to convert a ventricular tachycardia (VT) to normal sinus rhythm. Many embodiments of the present invention relate to the use of bi-ventricular (BV) ATP.

According to an embodiment of the present invention, the first pair of electrodes are shorted together to produce a unipolar electrode. The first anti-tachycardia pacing pulses are then delivered to the left ventricle using the shorted together first pair of electrodes. The first pair of electrodes include, for example, a left ventricular (LV) tip electrode and a LV ring electrode. Similarly, the second pair of electrodes can be shorted together prior to delivering the second anti-tachycardia pacing pulses to the right ventricle (i.e., using the shorted together second pair of electrodes). The second pair of electrodes include, for example, a right ventricular (RV) tip electrode and a RV ring electrode. In another embodiment, the RV tip electrode, the RV ring electrode and a RV coil electrode are all shorted together to produce an even larger electrode. The second anti-tachycardia pacing pulses are then delivered to the right ventricle using the shorted together RV tip, ring and coil electrodes.

An embodiment of the present invention includes sensing a signal using a pair of electrodes implanted in a ventricle of a patient's heart, and then shorting together the pair of electrodes. Anti-tachycardia pacing pulses are then delivered to the ventricle using the shorted together pair of electrodes. Timing of at least one of the pacing pulses is based on the sensed signal. The pair of electrodes can be a left ventricular (LV) tip electrode and an LV ring electrode implanted in the left ventricle. The pair of electrodes can alternatively be a right ventricular (RV) tip electrode and an RV ring electrode. An RV coil can also be shorted together with the RV tip and RV ring to provide an even larger electrode. The electrodes can be un-shorted after delivery of the unipolar pulses.

In an embodiment of the present invention, the pacing pulses delivered to the right ventricle have an opposite polarity compared to the pacing pulses delivered to the left ventricle.

BRIEF DESCRIPTION OF THE DRAWINGS/FIGURES

Further features and advantages of the present invention may be more readily understood by reference to the following description taken in conjunction with the accompanying drawings, in which.

DETAILED DESCRIPTION OF THE INVENTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

I. Exemplary Stimulation Device

Figure 1:
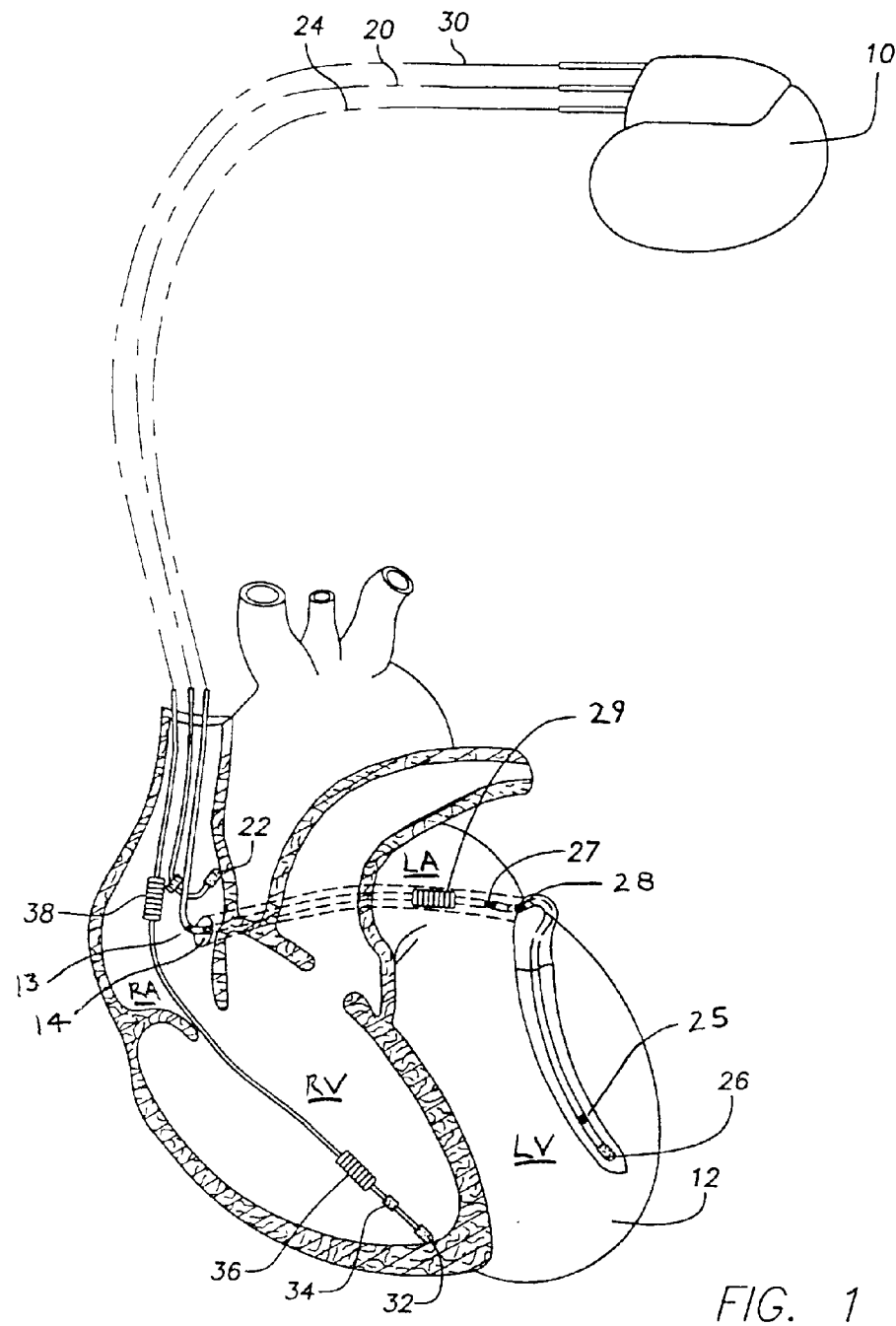
FIG. 1 is a simplified diagram illustrating an exemplary implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. Stimulation device 10 is also known as and referred to as a pacing device, a pacing apparatus, a cardiac rhythm management device, or an implantable cardiac stimulation device. Stimulation device 10 can be an implantable cardioverter/defibrillator (ICD).

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using a left ventricular (LV) tip electrode 26 and a LV ring 25. Left atrial pacing therapy uses, for example, first and second left atrial (LA) ring electrodes 27 and 28. Shocking therapy can be performed useing at least a left atrial (LA) coil electrode 29. For a description of an exemplary coronary sinus lead, see U.S. patent application Ser. No. 09/196,898, "A Self-Anchoring Coronary Sinus Lead" (Pianca et al.), and U.S. Pat. No. 5,466,254, "Coronary Sinus Lead with Atrial Sensing Capability" (Helland), which patent documents are incorporated herein by reference. Coronary sinus lead 24 can also include a pair of right atrial (RA) rings 13 and 14 that may be used to provide right atrial chamber pacing therapy, as shown in FIG. 1.

The stimulation device 10 is also shown in electrical communication with the patient's heart 12 by way of an implantable right ventricular lead 30 having, in this embodiment, an RV tip electrode 32, an RV ring electrode 34, an RV coil electrode 36, and a superior vena cava (SVC) coil electrode 38 (also known as a right atrial (RA) coil electrode). Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
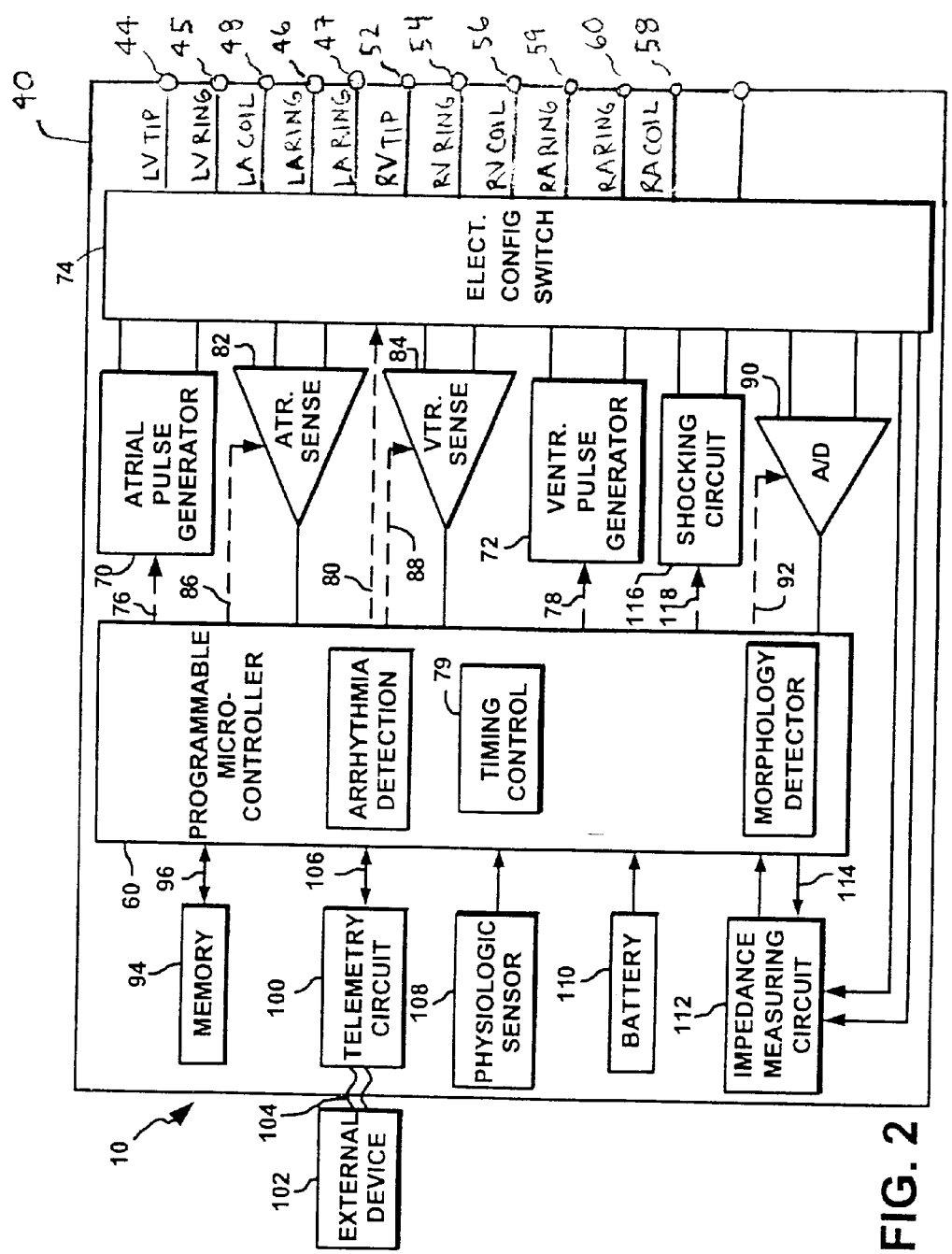
FIG. 2 is a functional block diagram of the multi-chamber implantable stimulation device of FIG. 1 illustrating the basic elements of the stimulation device which can provide cardioversion, defibrillation and pacing stimulation in four chambers of the heart.

FIG. 2 illustrates a simplified block diagram of the exemplary multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 29, 36 and 38 of FIG. 1, for shocking purposes. The housing 40 further includes a connector (not shown) having a plurality of terminals, 44, 45, 46, 47, 48, 52, 54, 56, 58, 59 and 60 (shown schematically and, for convenience, the names of the electrodes to which they are connected are shown next to the terminals). As such, to achieve right atrial sensing and pacing, the connector includes, for example, a pair of right atrial ring terminals 59 and 60 that are respectively adapted for connection to first right atrial (RA) ring electrode 13 and second RA ring electrode 14.

To achieve left chamber sensing, pacing and shocking, the connector includes, for example, a left ventricular tip terminal 44, a left ventricular ring terminal 45, a pair of left atrial ring terminals 46 and 47, and a left atrial shocking terminal 48, which are adapted for connection to the LV tip electrode 26, the LV ring electrode 25, first LA ring electrode 27 and second LA ring electrode 28, and LA coil electrode 29, respectively.

To support right chamber sensing, pacing and shocking, the connector further includes, for example, a right ventricular tip terminal 52, a right ventricular ring terminal 54, a right ventricular shocking terminal 56, and an SVC shocking terminal 58, which are adapted for connection to the RV tip electrode 32, RV ring electrode 34, the RV coil electrode 36, and the SVC coil electrode 38 (also know as RA coil electrode 38), respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74 (also referred to as switch bank 74). It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which are well known in the art.

The switch bank 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not specifically shown).

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. For a complete description of a typical sensing circuit, see U.S. Pat. No. 5,573,550, entitled "Implantable Stimulation Device having a Low Noise, Low Power, Precision Amplifier for Amplifying Cardiac Signals" (Zadeh et al.), which is incorporated herein by reference. The outputs of the atrial and ventricular sensing circuits, 82 and 84, are connected to the microcontroller 60 which, in turn, is able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, the polarization charge removal circuitry (not shown), and the timing of any blocking circuitry (not shown) coupled to the inputs of the sensing circuits,82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is the receipt or noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60, or other detection circuitry, for detecting an evoked response from the heart 12 in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days after implantation of the ICD) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Mann et al.), which patents are incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store a relatively large amount of data (e.g., from the data acquisition system 90), which data may then be used for subsequent analysis to select, for example, a pacing configuration, as described below.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. If the stimulation device 10 employs shocking therapy, then the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most current devices.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown for only completeness.

If stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial (LA) coil electrode 29, the RV coil electrode 36, and/or the SVC coil electrode 38. As noted above, the housing 40 may act as an active electrode in combination with the RV coil electrode 36, or as part of a split electrical vector using the SVC coil electrode 38 or the LA coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized to detect), and pertaining exclusively to the treatment of fibrillation. Accordingly, the microcontroller 60 is capable of controlling the synchronous or asynchronous delivery of the shocking pulses.

II. Discussion of Tachycardias

Before further explaining the present invention, it is helpful to briefly review the basic electrophysiologic mechanisms responsible for ventricular tachycardias (VTs).

During the normal cardiac cycle, a cardiac cell membrane depolarizes and repolarizes in a characteristic fashion known as the action potential. Action potential propagation occurs when depolarization in one cell generates current to neighboring cells, forcing membrane sodium channels to open and allowing a rapid excitatory influx of sodium that further depolarizes the membrane. Sodium channels then close. Other ionic currents repolarize the membrane to its resting state over a slow time course that is sufficiently long for sodium channels to recover excitability. Heart rate is important in this process because the interval between recovery in one cycle and activation in the next provides time for the cell to achieve ionic, metabolic and energetic equilibrium.

When cells die in a myocardial infarct, they electrically uncouple from neighboring viable cells, making the infarct completely inexcitable. Intrinsic or paced wavefronts encountering such an obstacle generally split into two components that collide and recombine on the opposite side of the infarct. When tissue adjacent to the infarct excites prematurely, however, reentry can result if one of the wavefronts blocks in a region with reduced excitability, i.e. incomplete sodium channel opening. The reduced excitability can result from inhomogeneities in membrane properties, geometric changes that increase the wavefront's electrical load, or incomplete recovery of excitability during a short interval. When blocking of one wavefront occurs, the other wavefront may be able to reenter the initial block site, causing was in known as a "reentrant circuit." Action potentials will continually propagate around the infarct at a rate considerably faster than the heart's intrinsic rate provided the reentrant wavefront, i.e. the head, moves slowly enough that tissue ahead recovers excitability, i.e. a tail can form. The spatial extent of inexcitable tissue in this circuit is termed the reentrant wavelength, and is approximated by the product of the head's velocity and the action potential duration. As long as the wavelength is less than the obstacle's perimeter, i.e. the reentrant path length, the head and tail remain separated by an excitable gap. Termination of anatomic reentry requires elimination of the excitable gap, which can be achieved by appropriate pacing. An appropriately timed stimulus (i.e., a pacing pulse) will initiate action potentials that propagate in both directions, colliding with the head and blocking in the tail. One of the objects of the present invention is to provide improved methods and apparatuses to terminate anatomic reentry.

In more simplified terms, the reentrant circuit can be thought of as a conduction wavefront propagating along a tissue mass of somewhat circular geometry. This circular conduction will consist of a portion of refractory tissue and a portion of excitable tissue. To terminate the circuit, a pacing stimulas should be provided at the time and location when the tissue just comes out of refractoriness. If this occurs, the paced stimulation wavefront proceeds toward the advancing wavefront of the circuit, colliding with the wavefront and interrupting the circuit. If the pacing stimulus (i.e., pacing pulse) arrives too soon it will be ineffective because the tissue will still be in refractoriness. If the stimulas arrives too late, it will generate wavefronts both towards the advancing wavefront and towards the tail of the circuit. Although one pacing generated wavefront will collide with the advancing wavefront of the reentrant circuit and will halt is progress, the latter pacing generated wavefront will act to sustain the reentrant circuit.

Accordingly, the probability of ATP succeeding is terminating the VT is related to the ability of the pacing stimulation wavefront to arrive at the location of the reentant circuit (e.g., within a myocardium) in such a manner that the reentrant circuit is modified or interrupted. Factors influencing this process include the distance of the pacing electrode (s) from the reentrant circuit, the pacing stimulas energy, and the timing of the pacing stimuli relative to the conduction velocities and refractory periods of the myocardium.

There are several different pacing modalities which have been suggested for termination of tachycardia. The underlying principle in all of them is that if a pacing stimuli stimulates the heart at least once shortly after a heartbeat, before the next naturally occurring heartbeat at the rapid rate, the heart may successively revert to sinus rhythm. Tachycardia is often the result of electrical feedback within the heart; a natural beat results in the feedback of an electrical stimulus which prematurely triggers another beat. By appropriately interposing a stimulated heartbeat, the stability of the feedback loop is disrupted.

III. Overview of the Present Invention

As discussed above, there is a need for improved methods and apparatuses for decreasing the failure rate of ATP. Referring back to FIG. 1, exemplary pacing device 10 is shown as including many electrodes. In the right ventricle— are the RV coil 36, the RV ring 34 and the RV tip 32. In the coronary sinus—are a pair of left atrial (LA) rings 27 and 28, the LV ring 25, and the LV tip 26. In the right atrium is the right atrial (RA) coil 38 and a pair of RA rings 13 and 14. The present invention uses novel combinations of these electrodes to achieve more effective ATP. The present invention also uses novel timing schemes to increase the effectiveness of ATP. The present invention also enables the use of multiple different pacing schemes. For example, the present invention enables the use of multiple different pacing protocols and/or multiple different electrode configurations. The present invention further provides for selection of one of multiple different ATP schemes.

IV. Embodiments of the Present Invention

A. Indepentent Bi-ventricular Pacing

As mentioned above, there are several different ATP modalities which have been suggested for termination of tachycardia, with the underlying principle being to stimulate the heart (i.e., using a pacing pulse) at least once shortly after a heartbeat, before the next naturally occurring heartbeat at the rapid rate, in an attempt to convert the tachycardia to sinus rhythm. In a first embodiment of the present invention, pacing pulses are independently produced using a left ventricular (LV) pace/sense electrode pair (e.g., LV ring 25 and LV tip 32), and a right ventricular (RV) pace/sense electrode pair (e.g., RV ring 34 and RV tip 32). Stated another way, in the first embodiment of the present invention, the RV is paced independently from the pacing of the LV.

The most common form of ATP is burst pacing, which delivers multiple pacing pulses (i.e., a burst of pulses) at a cycle length between 50 and 100% (and more typically between 70 and 90%) of the tachycardia cycle length. Delivering pulses having, for example, an 80% cycle length, is also known as delivering pulses having an 80% coupling interval. Each burst of pacing pulses typically includes 2–20 pulses. The number of bursts used is typically 1–15. The rate of each burst can either be a fixed predetermined rate (i.e., fixed burst) or a rate that is calculated based on the rate of the VT being treated (adaptive burst). Acceleration risk is minimized by keeping the number of pulses in a burst, the rate of the burst, and the number of bursts to the minimum required to terminate the VT. Many ATP regimens employ variations on this basic theme of burst pacing. As mentioned above, an aspect of the present invention is that the RV and LV are paced independent of one another. This can be accomplished, for example, by triggering the LV pace/sense electrode pair (e.g., LV ring 25 and LV tip 26) based on a sensed signal produced by the LV pace/sense pair, and triggering the RV pace/sense electrode pair (e.g., RV ring 34 and RV tip 32) based on a separate sensed signal produced by the RV pace/sense pair. This means that the timing of at least a first pacing pulse (e.g., in a burst of anti-tachycardia pacing pulses) is based on the corresponding sensed signal. Timing of additional pulses (e.g., in the burst) can also be based on the sensed signal. Alternatively, timing of additional pulses can be based on a predetermined or calculated coupling interval. This shall now be explained in more detail with Reference to FIG. 3.

Figure 3:
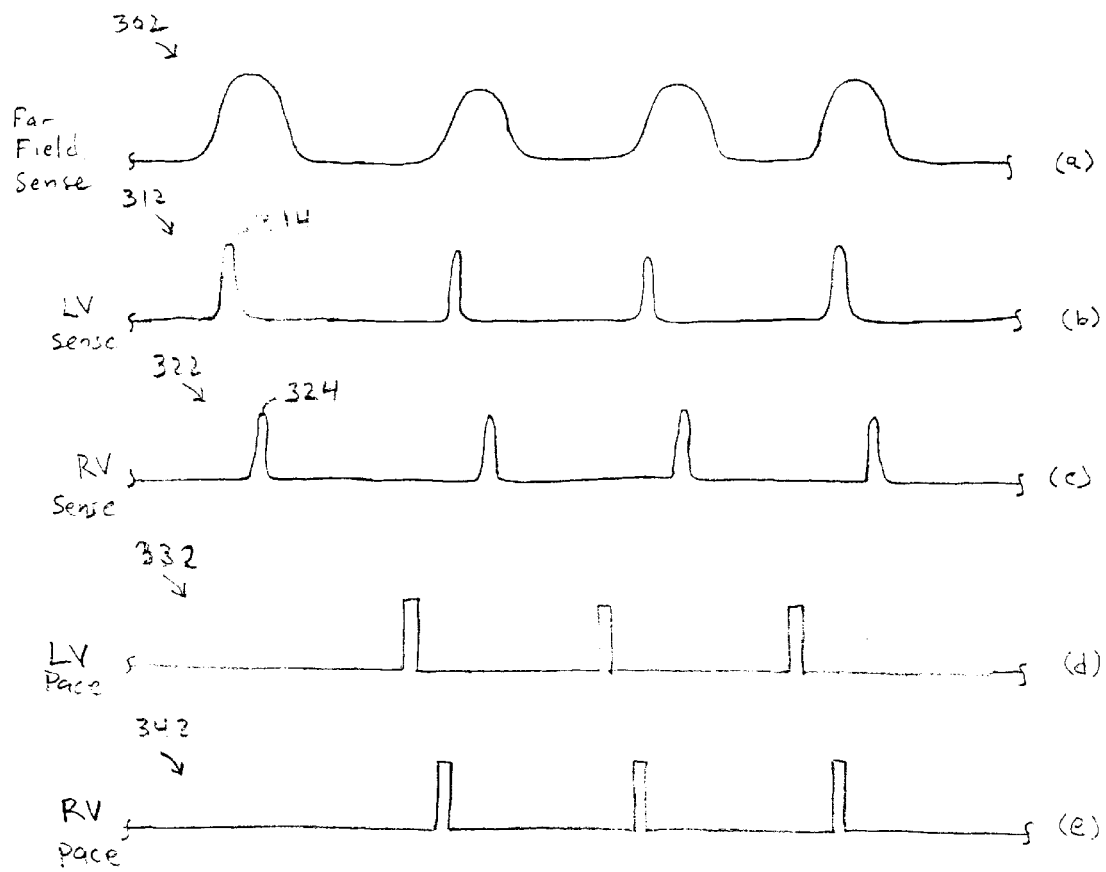
FIG. 3 illustrates an exemplary waveform corresponding to a far field signal, an exemplary waveform corresponding to a signal sensed in the left ventricle, an exemplary waveform corresponding to a signal sensed in the right ventricle, an exemplary left ventricle and right ventricle pacing signal.

Referring to FIG. 3, waveform (b.) shows an exemplary sensed signal 312, picked up (i.e., sensed) by the LV pair, during tachycardia. Waveform (c.) shows an exemplary sensed signal 322, picked up by the RV pair, during the same tachycardia. In this example the location of the reentrant loop is closer to the LV pair than to the RV pair. Accordingly, as is apparent from waveforms (b.) and (c.), the reentrant loop is sensed sooner (i.e., earlier) at the LV pair. This embodiment of the present invention takes this into account when performing ATP. More specifically, rather than generating simultaneous right ventricle and left ventricle pulses (i.e., simultaneous bi-ventricular pulses), independent LV pacing pulses and RV pacing pulses are generated, as shown by waveforms (d) and (e). Waveform (d) shows the a left ventricle pacing signal 332, for example, representing the voltage between LV ring 25 and LV tip 26. Waveform (e) shows the right ventricle pacing signal 342, for example, representing the voltage between RV ring 34 and RV tip 36. In one embodiment, the coupling interval(s) of the LV pacing pulses generated by the LV electrode pair are the same as the coupling interval(s) of the RV pacing pulses generated by the LV electrode pair. Alternatively, the coupling interval(s) of the LV pacing pulses generated by the LV electrode pair can be different than the coupling interval(s) of the RV pacing pulses generated by the LV electrode pair. Thus each pacing pair does its independent sensing and pacing with optimal timing.

Figure 4:
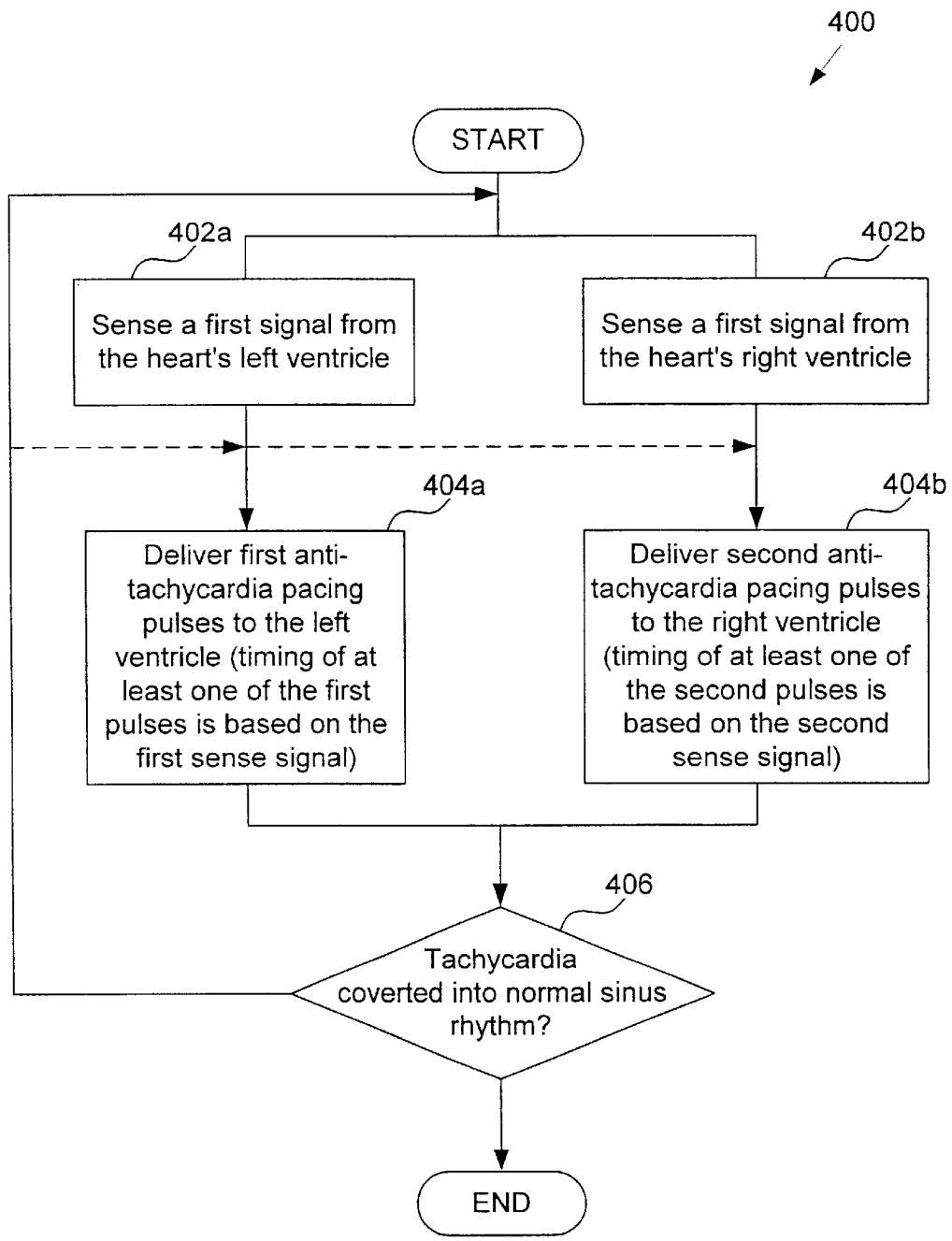
FIG. 4 is a flowchart describing a method for independent bi-ventricular anti-tachycardia pacing, according to an embodiment of the present invention.

These embodiments are further explained with reference to the flow chart of FIG. 4, which outlines a method 400 of the present invention that can be implemented in an embodiment of device 10. In this flow chart, and the other flow charts described herein, the various algorithmic steps are summarized in individual "blocks." Such blocks describe specific actions or decisions that are carried out as the algorithm proceeds. Where a microcontroller (or equivalent) is employed, the flow charts presented herein provide the basis for a "control program" that may be used by such a microcontroller (or equivalent) to effectuate the desired control of the pacing device. Those skilled in the art may readily write such a control program based on the flow charts and other descriptions presented herein.

Method 400 is used in response to the detection of a ventricular tachycardia. At a step 402a a first signal (e.g., sensed signal 312) is sensed in the heart's left ventricle. At a step 402b (e.g., sensed signal 322) a second signal is sensed in the heart's right ventricle. At a step 404a, first antitachycardia pacing pulses are delivered to the left ventricle. The first time step 404a is performed, timing of at least one of the first pulses is based on the first sensed signal. At a step 402b, second anti-tachycardia pacing pulses are delivered to the right ventricle. The timing of at least one of the second pulses is preferably based on the second sensed signal. Notice that steps 402a and 404a are shown as occurring in parallel with, but independently of, steps 402b and 404b.

At a next step 406, there is a determination whether the ventricular tachycardia has been converted into normal sinus rhythm. If the tachycardia has been converted, then method 400 ends. If the tachycardia persists (i.e., has not been converted to normal sinus rhythm), then flow returns to steps 402a and 402b, as shown in FIG. 4. Accordingly, first and second sensed signals can again be produced (i.e., sensed), and used for timing additional anti-tachycardia pacing pulses. Alternatively, if the tachycardia persists, flow can return to steps 404a and 404b, as shown in dashed line. The timing of additional pacing pulses can at this point be based on predetermined or calculated coupling intervals.

B. Pacing First with the Electrodes Closer to Reentrant Loop

Figure 5:
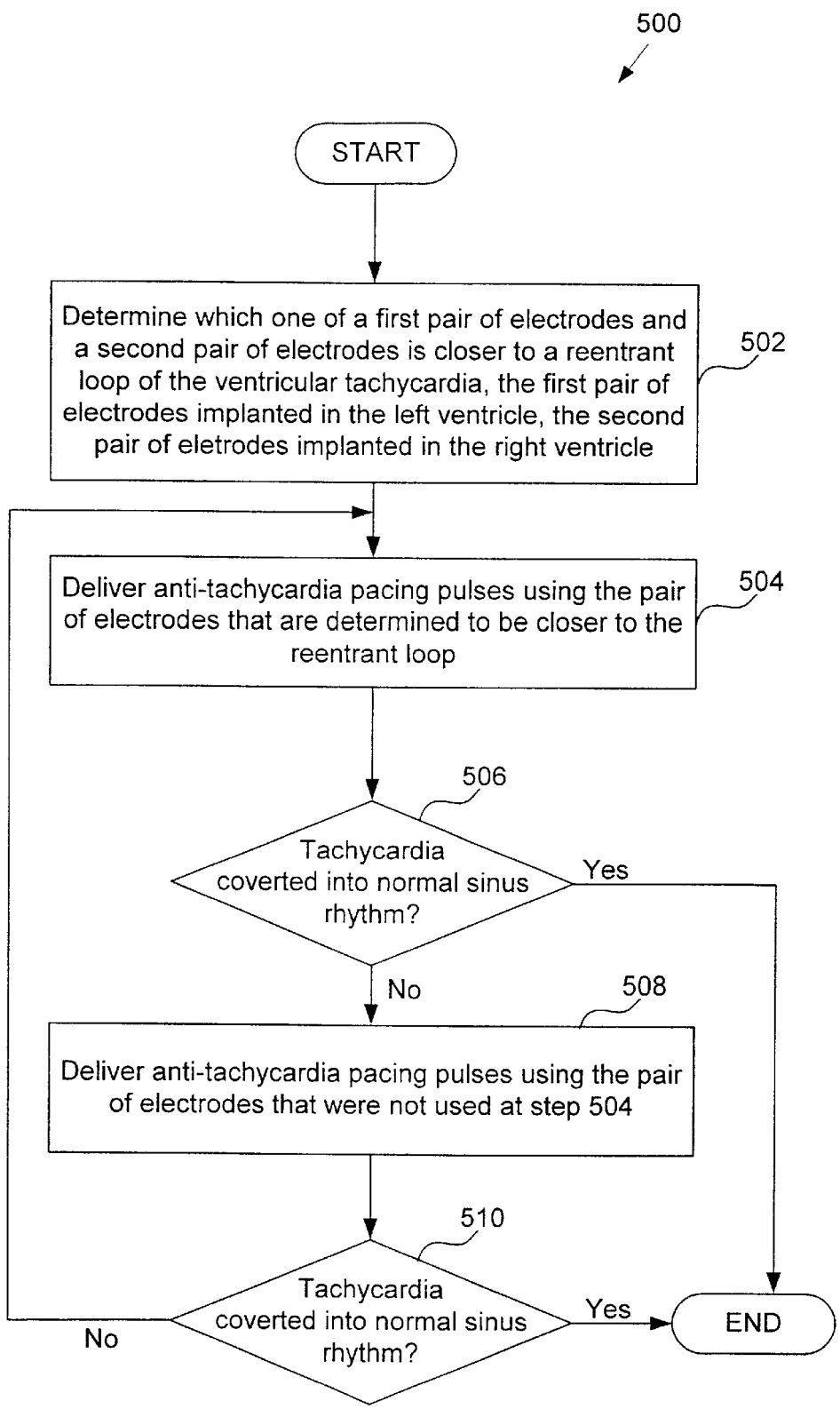
FIG. 5 is a flowchart describing a method for anti-tachycardia pacing where a pair of electrodes that are determined to be closer to the reentrant loop are used first to deliver pacing pulses, according to an embodiment of the present invention.

According to an embodiment of the present invention, electrodes that are closest to the reentrant loop are used first to attempt to convert a ventricular tachycardia to normal sinus rhythm. This embodiment can be explained with reference to the flowchart of FIG. 5, which outlines a method 500 of the present invention that can be implemented in an embodiment of device 10. Method 500 is used in response to the detection of a ventricular tachycardia. At a first step, 502, there is a determination of which one of a first pair of electrodes (e.g., LV ring 25 and LV tip) and a second pair of electrodes is closer to a reentrant loop of the ventricular tachycardia, where the first pair of electrodes are implanted in the left ventricle, and the second pair of electrodes are implanted in the right ventricle. Additional details of this step are discussed below. For each of the embodiments discussed herein, it is noted that "electrodes implanted in the left ventricle" is meant to include electrodes on the surface of the left ventricle, such as in the veins of the left ventricle.

At a next step 504, anti-tachycardia pacing (ATP) pulses are delivered using the pair of electrodes that are determined to be closer to the reentrant loop. According to one embodiment, ATP pulses are only delivered using the electrodes that are closer to the reentrant loop.

In an alternative embodiment, the other pair of electrodes (i.e., those not closest to the reentrant loop) are used to deliver ATP pulses if the tachycardia was not converted into normal sinus rhythm. More specifically, at a next step 506, there is a determination whether the ventricular tachycardia has been converted into normal sinus rhythm. If the tachycardia has been converted, then method 500 ends. If the tachycardia persists (i.e., has not been converted to normal sinus rhythm), then, at a step 508, anti-tachycardia pacing pulses are delivered using the pair of electrodes that were not used at step 504. Next, at a step 510, there is another determination of whether the ventricular tachycardia was converted into normal sinus rhythm. If the tachycardia as been converted, then method 500 ends. However, if the tachycardia persists than flow returns to step 504.

There are various ways that step 502 can be accomplished. Referring back to FIG. 3, in one embodiment, a first signal (e.g., 312) is sensed from a heart's left ventricle (e.g., using a pair of electrodes implanted in the left ventricle), and a second signal (e.g., 322) is sensed from the heart's right ventricle (e.g., using a pair of electrodes implanted in the right ventricle). The terms "first" and "second" as used herein are not meant to signify an order (unless specifically specified to), but rather, are meant to distinguish signals sensed by different electrodes. These first and second sensed signals (e.g., 312 and 322) are offset in time from one another, as shown in waveforms (b) and (c), even though they are sensing the same electrical activity. The reason these signal are offset from one another is due to the different distances the electrodes are from the reentrant loop. The determination of which one of the first pair of electrodes and the second pair of electrodes are closer to the reentrant loop of the ventricular tachycardia can be based on the first and second sensed signals (e.g., 312 and 322). For example, a corresponding pair of sensed pulses (e.g., 314 and 324) can be compared. It can be assumed that the pair of electrodes that sensed the earlier pulse (e.g., 314) of a corresponding pair or pulses (e.g., 314 and 324) is the closer pair of electrodes (e.g., the left ventricular electrode pair).

In another embodiment, in addition to sensing a first sensed signal (e.g. 312) and a second sensed signal (e.g., 322), a far field signal is also sensed. Waveform (a.) of FIG. 3 shows an exemplary far field signal 302 representing, for example, the voltage between RV coil 36 and housing 40 (also known as the "can", "case" or "case electrode"). According to an embodiment of the present invention, a determination of whether the reentrant loop is closer to the LV electrodes or RV electrodes is based on far field signal 302. More specifically, if the beginning of the far field pulse (i.e., the portion that begins to go positive) is closer to an LV sensed pulse (e.g., of sensed signal 312), then it is assume that the reentrant loop is closer to the LV electrodes. If the beginning of the far field pulse (i.e., the portion that begins to go positive) is closer to an RV sensed pulse (e.g., of sensed signal 322), then it is assume that the reentrant loop is closer to the RV electrodes. From exemplary waveforms (a), (b) and (c) of FIG. 3, it can thus be determined that the reentrant loop is closer to the left ventricular pair.

C. Unipolar Pacing

In another embodiment of the present invention, unipolar BV pacing is used. A potential problem with bipolar pacing is that the "reach" of the electric field is relatively small because it is tightly confined between the two electrodes of an electrode pair (e.g., the LV pair or RV pair). According to an embodiment of the present invention, the tip and ring of one or more electrode pairs are shorted together, during pacing, to acts as a large unipolar pacing lead. For example, LV ring 25 and LV tip 26 are shorted together and/or RV ring 34 and the RV tip 32 are shorted together. In specific embodiments, when the LV ring 25 and LV tip 26 are shorted together to form a unipolar pacing lead, the return electrode (s) can be, for example: one of the RV ring 34 and RV tip 32; the can 40; or the RV ring 34 and RV tip 32 shorted together.

The shorting can be performed, for example, within the electrode configuration switch 74. As mentioned above, electrode switch 74 can be controlled by microcontroller 60, via control signal 80. The effectively larger lead (i.e., the lead produced by shorting together two electrodes) is less efficient and is probably not suitable for chronic pacing. However, in spite of its reduced electrical efficiency, the shorted unipolar pacing lead will stimulate many more cardiac cells, thereby increasing the chance of crossing through the wavefronts to terminate the tachycardia.

A shorted electrode pair of the present invention can be used for single ventricular pacing. Alternatively, shorted electrode pairs of the present invention can be used during simultaneous BV pacing (i.e., where the pacing pulse produced by the LV pair is synchronous with the pacing pulse produced by the RV pair). Alternatively, shorted electrode pairs of the present invention can be used during independent BV pacing of the present invention, which has been described above.

Figure 6:
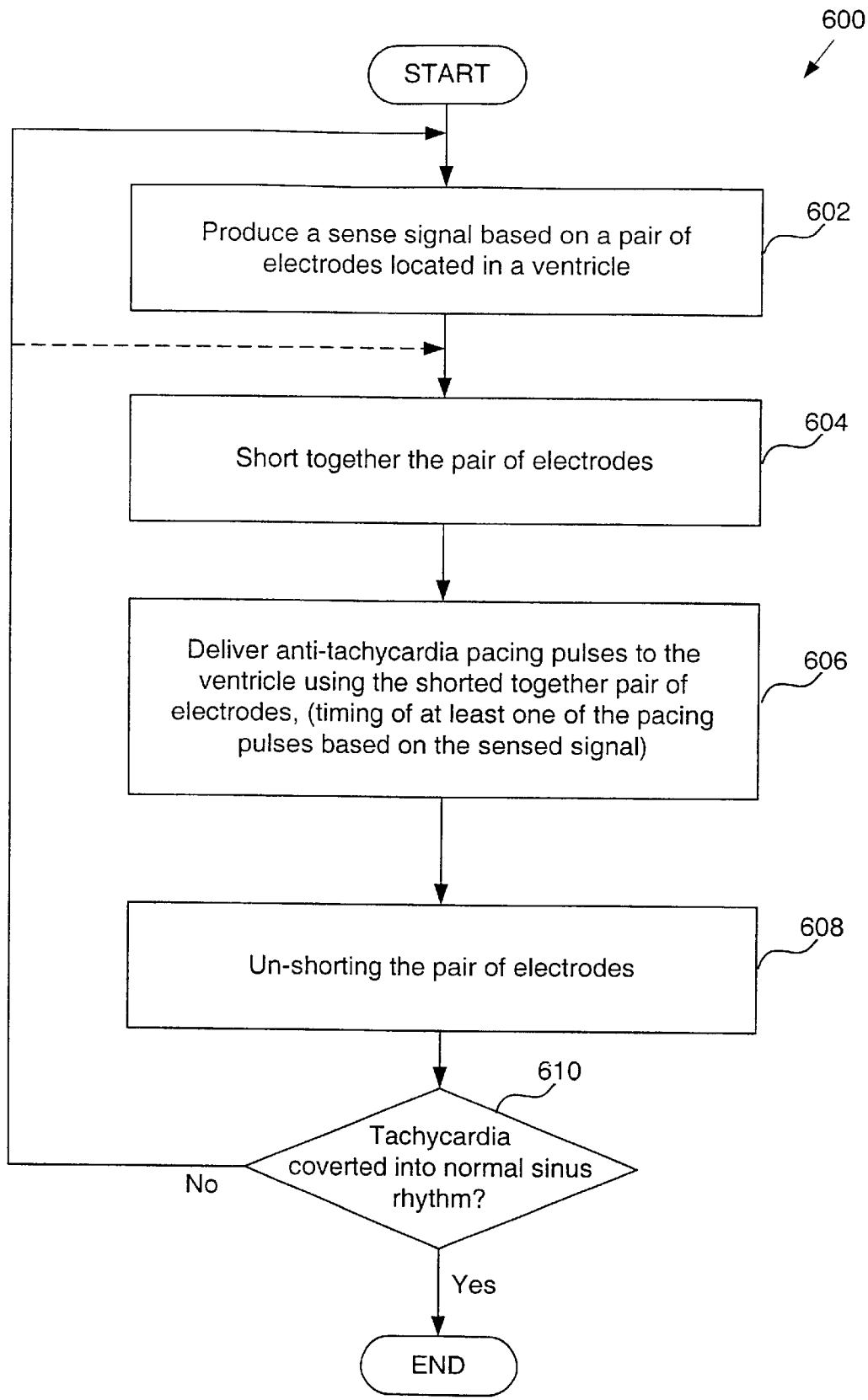
FIG. 6 is a flowchart describing a method for unipolar pacing, according to an embodiment of the present invention.

These embodiments can be explained with reference to the flowchart of FIG. 6, which outlines a method 600 of unipolar pacing according to the present invention. Method 600 is used in response to the detection of a ventricular tachycardia.

At a step 602, a sensed signal is produced based on a pair of electrodes implanted in a ventricle. This can be the same sensed signal that was used to detect the ventricular tachycardia, or this signal can be sensed after the tachycardia is detected. The pair of electrodes are, for example, RV tip electrode 22 and RV ring electrode 34. Alternatively, the pair of electrodes are LV tip electrode 26 and LV ring electrode 25.

At a next step 604, the pair of electrodes are shorted together, to essentially form a unipolar electrode. As mentioned above, the shorting can be performed, for example, within the electrode configuration switch 74 as controlled by microcontroller 60.

Then, at a step 606, anti-tachycardia pacing pulses are delivered to the ventricle using the shorted together pair of electrodes. The first time step 606 occurs following detection of a tachycardia, timing of at least one of the pacing pulses (e.g., a first one of the pacing pulses) is based on the sensed signal.

At a next step 608, the pair of electrodes are un-shorted. Once unshorted, the pair of electrodes can be used to detect the electrical characteristics in the heart. The un-shorted electrodes can then be used to determine whether the tachycardia has been converted to normal sinus rhythm, at a step 610. Alternatively or additionally, another pair of electrodes can be used to determine whether the tachycardia has been converted to normal sinus rhythm.

If the tachycardia has been converted, then method 600 ends. If the tachycardia persists, then flow returns to step 602. If a signal was sensed to perform step 610, then steps 602 and 610 can be combined into one step. Flow may alternatively return directly to step 604, as shown in dashed line.

In another embodiment of the present invention, more than two electrodes are shorted together at step 504. This will provide for an effectively larger unipolar electrode. For example, RV tip 32, RV ring 34 and RV coil 36 can all be shorted together to produce an effectively very large unipolar electrode. This very large unipolar electrode will stimulate even more cardiac cells, thereby further increasing the chance of crossing through the wavefronts to terminate the tachycardia.

D. Unipolar BV Pacing with Leads of Opposite Polarities

A problem with unipolar pacing is that the current from the can to the pacing electrodes can result in pocket stimulation at the site of the can (i.e., stimulation of muscle tissue surrounding the can). Pocket stimulation, although not dangerous, can be uncomfortable to a patient. In an embodiment of the present invention, pacing pulses generated by a unipolar LV electrode (e.g., produced by shorting together LV ring 25 and LV tip 26) have an opposite polarity than pacing pulses generate by an RV unipolar electrode (e.g., produced by shorting together the RV ring 54 and RV tip 52) when performing BV ATP. This would result in an almost zero net current flowing from the can, when the LV unipolar electrode pulses and RV unipolar electrode pulses are delivered simultaneously.

In one embodiment, the polarity of each unipolar electrode is constant and opposite the other unipolar electrode. In another embodiment, the polarity of a first unipolar electrode (e.g., produced by shorting together LV ring 25 and LV tip 26) alternates between a first polarity (e.g., positive) and a second polarity (e.g., negative), while the polarity of a second unipolar electrode (e.g., produced by shorting together RV ring 54 and RV tip 52) alternates between the second polarity (e.g., negative) and the first polarity (e.g., positive) such that each unipolar electrodes always has the opposite polarity of the other unipolar electrode. In other words, opposite polarities are used at different sites (e.g., the left ventricle and the right ventricle). The alternating could happen on a pulse by pulse basis. Alternatively, the alternating could happen on a pulse burst by pulse burst basis.

F. Multiple Pacing Configurations

According to an embodiment of the present invention, stimulation device 10 is adapted to be able to perform ATP using a plurality of different pacing configurations. Stimulation device can also be adapted to automatically change pacing configurations. Exemplary different pacing configurations include: pacing only the right ventricle; pacing only the left ventricle; and pacing the left ventricle and the right ventricle (i.e., bi-ventricular pacing). The bi-ventricular pacing configuration can include simultaneously pacing the left ventricle and the right ventricle, or alternatively, independently pacing the left ventricle and the right ventricle.

Figure 7:
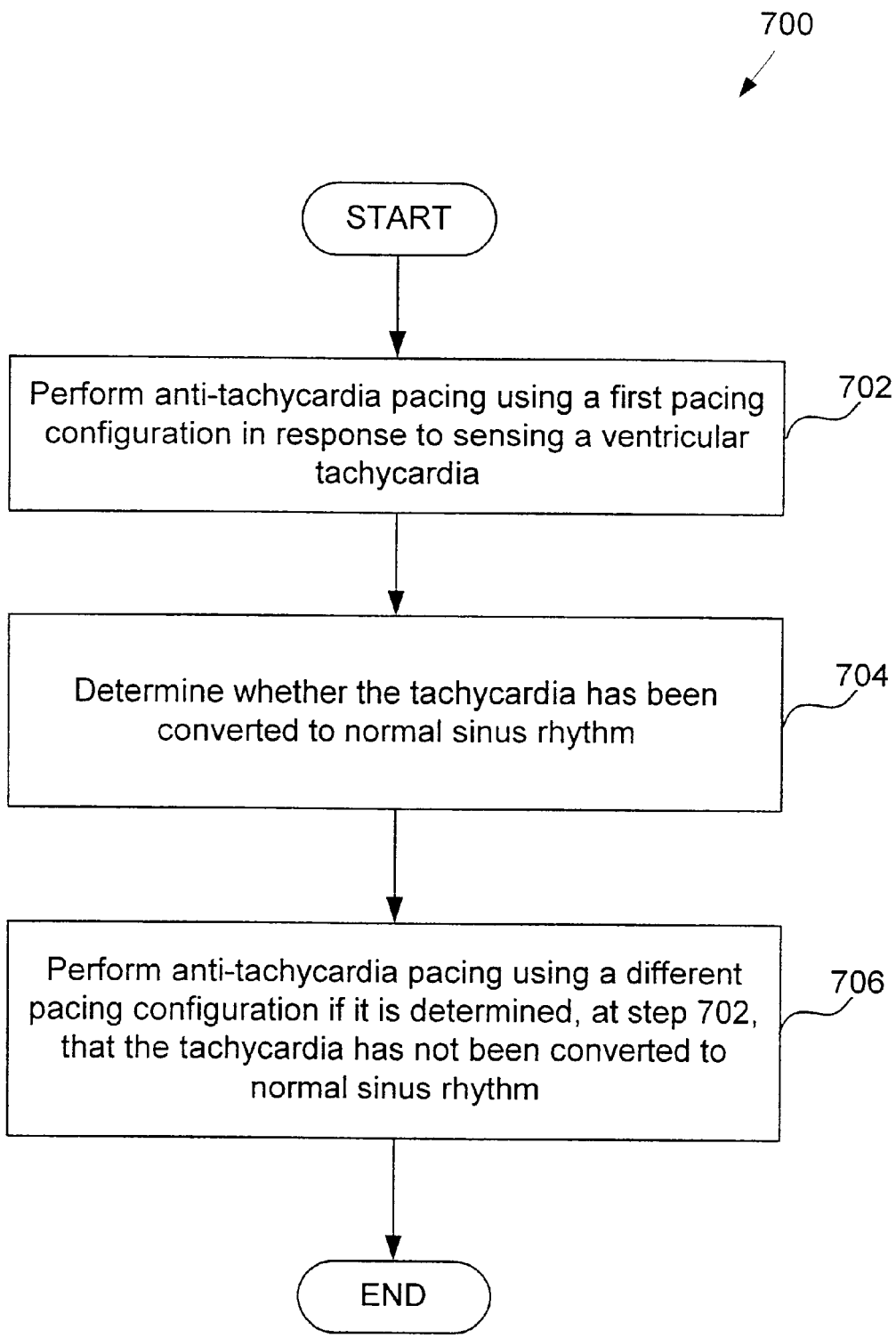
FIG. 7 is a flowchart describing a method for changing pacing configurations, according to an embodiment of the present invention.

This embodiment can be explained with reference to the flowchart of FIG. 7, which outlines a method 700 of changing pacing configurations. Method 700 is used in response to the detection of a ventricular tachycardia.

At a step 702, ATP pulses are delivered using a first pacing configuration in response to sensing a ventricular tachycardia.

At a next step 704, there is a determination of whether the tachycardia has been converted to normal sinus rhythm.

Then at a step 706, anti-tachycardia pacing is delivered using a different pacing configuration if it is determined, at step 704, that the tachycardia has not been converted to normal sinus rhythm.

According to an embodiment of the present invention, information is stored that identifies a pacing configuration that was used to successfully convert the ventricular tachycardia to normal sinus rhythm, in response to determining that the tachycardia has been converted to normal sinus rhythm. Then, in response to sensing another ventricular tachycardia, further antitachycardia pacing can be performed using the pacing configuration that was used to successfully convert the previous ventricular tachycardia to normal sinus rhythm.

The above described method 700 can alternatively be thought of in terms of electrode configurations. That is, the method can be for changing the electrode configuration used for anti-tachycardia pacing. Exemplary electrode configurations that can be used to deliver anti-tachycardia pacing pulses include electrodes implanted in the right ventricle; electrodes implanted in the left ventricle; and electrodes implanted in the right ventricle and electrodes implanted in the left ventricle. This method is for use in an implantable device capable of performing ATP using a plurality of different electrode configurations. In a first step, first ATP pulses are delivered in response to sensing a ventricular tachycardia. The first ATP pulses are delivered using a first electrode configuration. At a next step, there is a determination whether the tachycardia has been converted to normal sinus rhythm. Second ATP pulses are delivered using a different electrode configuration if it is determined that the tachycardia has not been converted to normal sinus rhythm.

Figure 8:
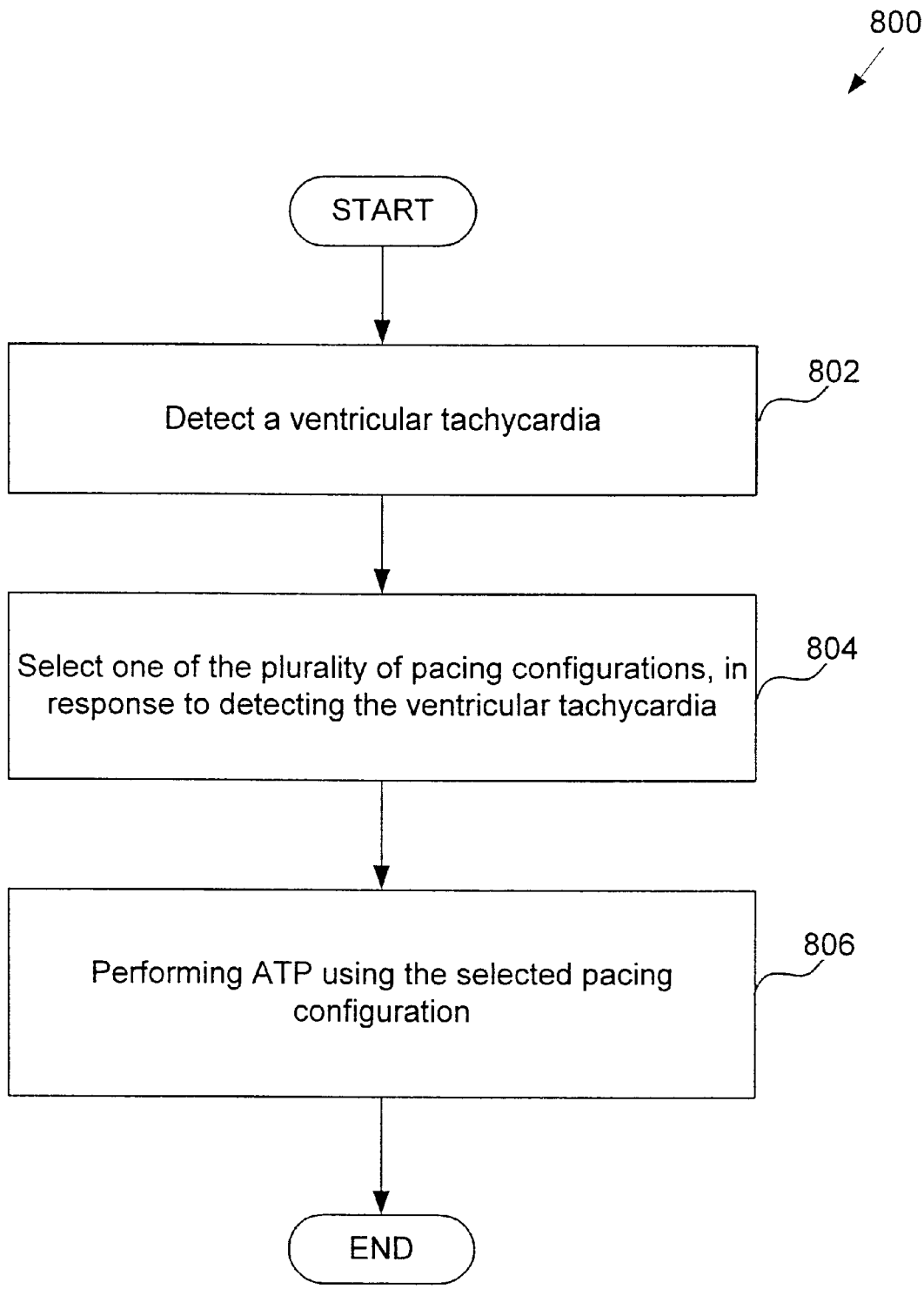
FIG. 8 is a flowchart describing a method for selecting a pacing configuration, according to an embodiment of the present invention.

As mentioned above, in an embodiment of the present invention one of a plurality of pacing configurations (or electrode configurations) can be selected based on stored information. This will be explained in more detail with reference to the flowchart of FIG. 8, which outlines a method 800 of selecting a pacing configuration. This method, like method 700, is for use in an implantable device capable of performing anti-tachycardia pacing using a plurality of different pacing configurations.

At a first step 802, a ventricular tachycardia is detected.

At a next step 804, one of the plurality of pacing configurations is selected, in response to detecting the ventricular tachycardia. The plurality of pacing configurations can include, for example: pacing only the right ventricle; pacing only the left ventricle; and pacing the left ventricle and the right ventricle (i.e., bi-ventricular pacing). Bi-ventricular pacing can include, for example, pacing the left and right ventricles simultaneously, or independently pacing the left and right ventricles. This step is described in more detail below.

Next, at a step 806, ATP is performed using the pacing configuration selected at step 804.

According to an embodiment of the present invention, the pacing configuration that is selected at step 804 is the configuration that was most recently used to successfully convert a previous ventricular tachycardia to normal sinus rhythm.

According to another embodiment of the present, step 804 includes the steps of: sensing a signal indicative of the detected tachycardia (e.g., using a pair of electrodes); and selecting one of the plurality of pacing configurations based on the shape (i.e., morphology) of the signal. For example, the selection is of the pacing configuration that was used to successfully convert a previous ventricular tachycardia associated with a similar signal shape. This is very useful in treating a heart that is susceptible to a tachycardia from different reentrant loops, each of which will produce a different signal indicative of the tachycardia. Selecting a pacing configuration that was previously successful to treat a tachycardia producing a similarly shaped sensed signal should reduce the amount of time it will take to convert the tachycardia to normal sinus rhythm. Exemplary devices and methods for morphology discrimination are disclosed in U.S. Pat. No. 5,240,009 (Williams) and U.S. Pat. No. 5,193,550 (Duffin), both of which are incorporated herein by reference.

According to an embodiment of the present invention, prior to step 802 the following steps of are performed. First, morphology information corresponding to at least two previous ventricular tachycardia episodes are stored (e.g., in memory 94). Additionally, configuration information that identifies corresponding pacing configurations that were used to successfully convert the at least two previous ventricular tachycardias to normal sinus rhythm are also stored (e.g., in memory 94). This information can then be used to assist in the selection made at step 804.

G. Adjusting a Time Offset

Figure 9:
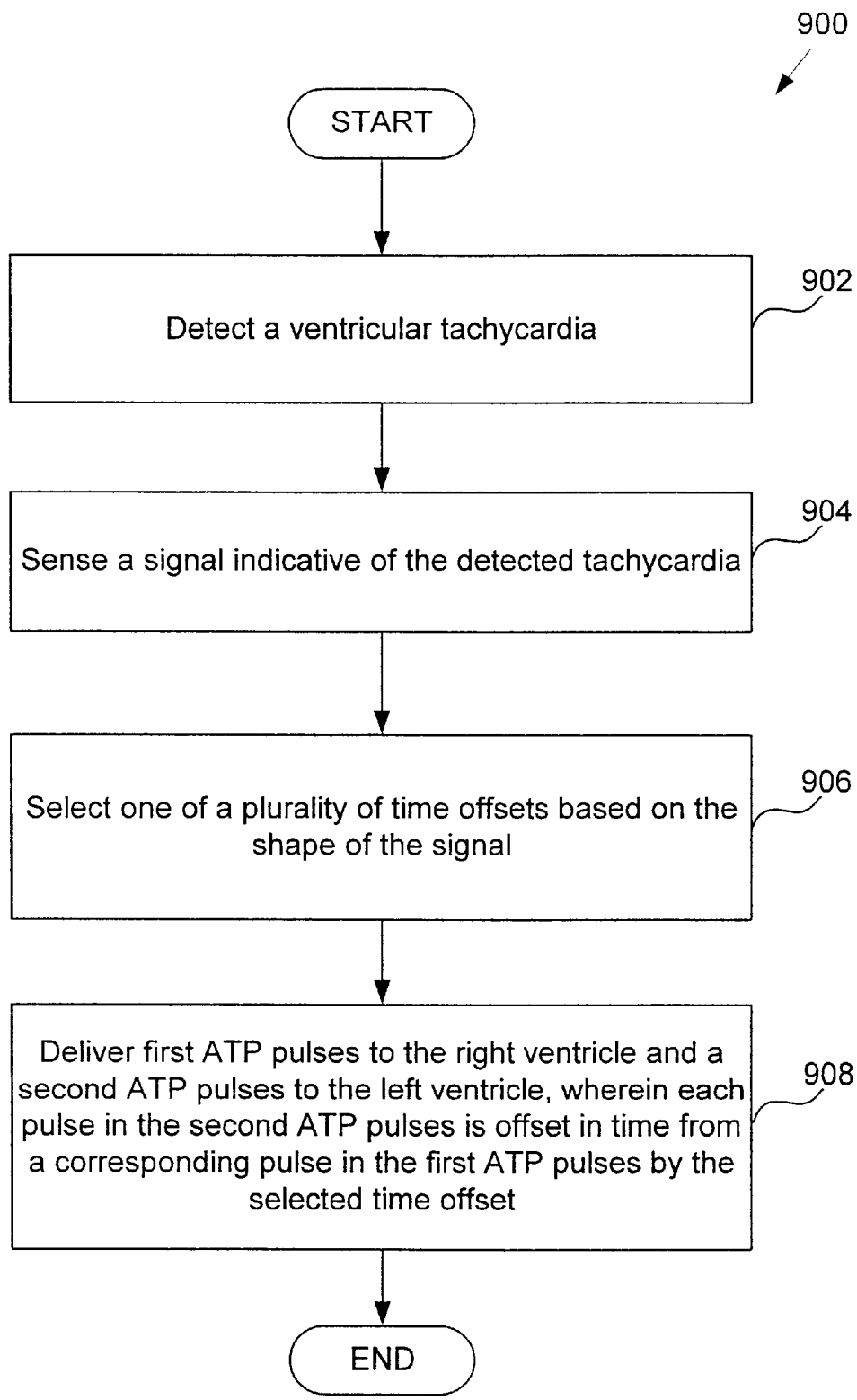
FIG. 9 is a flowchart describing a method for selecting a time offset between pacing pulses in different chambers of the heart, according to an embodiment of the present invention.

According to an embodiment of the present invention, one a plurality of time offsets between pacing pulses delivered in the right and left ventricles are selected. This embodiment, which is for use in an implantable device capable of performing bi-ventricular anti-tachycardia pacing (ATP), is described with reference to the flowchart of FIG. 9.

At a first step 902 of a method 900, a ventricular tachycardia is detected. Once the ventricular tachycardia is detected, the remaining steps of method 900 are performed. More specifically, at a next step 904, a signal indicative of the detected tachycardia is sensed. If the ventricular tachycardia is detected (at step 902) based on such a sensed signal, then steps 902 and 904 can be combined into one step.

At a next step 906, one of a plurality of different time offsets is selected based on the shape of the sensed signal. Each time offset defines a delay between an ATP pulse delivered to the right ventricle and a corresponding ATP pulse delivered the left ventricle during bi-ventricular ATP pacing. The time offsets can be positive or negative, to thereby specify which ventricle is paced first. For example, a positive time offset can specify that the right ventricle is paced first, where a negative time offset can specify that the left ventricle is paced first. Of course, the present invention is not limited to this example.

At a next step 908, first ATP pulses are delivered to the right ventricle and second ATP pulses are delivered to the left ventricle, wherein each pulse in the second ATP pulses is offset in time from a corresponding pulse in the first ATP pulses by the selected time offset. The terms "first" and "second" as used herein are not meant to signify an order (unless specifically specified to), but rather, are meant to distinguish ATP pulses delivered to different chambers.

According to an embodiment of the present invention, prior to step 902 the following steps of are performed. First, morphology information corresponding to at least two previous ventricular tachycardia episodes are stored (e.g., in memory 94). Additionally, configuration information that identifies corresponding time offsets that were used to successfully convert the at least two previous ventricular tachycardias to normal sinus rhythm are also stored (e.g., in memory 94). This information can then be used to assist in the selection made at step 906.

V. Conclusion

The previous description of the preferred embodiments is provided to enable any person skilled in the art to make or use the present invention. While the invention has been particularly shown and described with reference to preferred embodiments thereof, it will be understood by those skilled in the art that various changes in form and details may be made therein without departing from the spirit and scope of the invention.

Burst ATP pacing was mentioned above. However, the present invention is not limited to use with burst ATP pacing. Rather, embodiments of the present invention can also be used with other types of ATP pacing, such as, but not limited to, underdrive pacing, programmed extrastimuli (PES) and train pacing.

Many embodiment of the present invention can be combined. For example, the independent bi-ventricular ATP of the present invention can be performed using unipolar pacing (i.e., shorted together electrodes) of the present invention. For another example, ATP pulses can be delivered first to the electrodes that are closer to a reentrant loop, after shorting together the electrodes to produce a unipolar pacing electrode. In still another example, ATP can be performed using a pacing configuration that was previously used to successfully convert an earlier tachycardia producing a sensed signal having a similar morphology. The previous pacing configuration could be pacing the right ventricle using a unipolar electrode (e.g., produced by shorting together RV tip 32 and RV ring 34), pacing the left ventricle using a unipolar electrode (e.g., produced by shorting together LV tip 26 and LV ring 25) or bi-ventricular unipolar pacing. These are just a few examples that are not meant to be limiting.

Furthermore, embodiments of the present invention discussed above have been primarily described as methods with reference to flow charts. The present invention is also directed to devices (also referred to as apparatuses) that perform the features discussed above. For example, the present invention is also directed to a microprocessor (e.g., microprocessor 60) that performs the features of the present invention. Additionally, the present invention is also directed to an implantable device (e.g., pacing device 10) that includes a microprocessor for performing such features. Further, the present invention is also directed to systems that perform the features discussed above. Such a system can be, for example, an external processor in communications with a microprocessor of an implantable device.

What is claimed is:

1. A method for converting a ventricular tachycardia to normal sinus rhythm, comprising the steps of:

(a) sensing a signal using a pair of electrodes implanted in or adjacent a ventricle of a patient's heart;

(b) shorting together the pair of electrodes; and (c) delivering anti-tachycardia pacing pulses to the ventricle using the shorted together pair of electrodes, wherein timing of at least one of the pacing pulses is based on the sensed signal.

2. The method of claim 1, wherein the pair of electrodes comprise a left ventricular (LV) tip electrode and an LV ring electrode, and wherein:

step (a) comprises sensing the signal using the LV tip electrode and LV ring electrode implanted in or adjacent the heart's left ventricle;

step (b) comprises shorting together the LV tip electrode and the LV ring electrode; and step (c) comprises delivering anti-tachycardia pacing pulses to the left ventricle using the shorted together LV tip electrode and LV ring electrode.

3. The method of claim 1, wherein the pair of electrodes comprise a right ventricular (RV) tip electrode and an RV ring electrode, and wherein:

step (a) comprises producing the sensed signal using the RV tip electrode and RV ring electrode implanted in the heart's right ventricle;

step (b) comprises shorting together the RV tip electrode and the RV ring electrode; and step (c) comprises delivering anti-tachycardia pacing pulses to the right ventricle using the shorted together RV tip electrode and RV ring electrode.

4. The method of claim 1, further comprising the step of:
(d) un-shorting the pair of electrodes.

5. The method of claim 4, further comprising the step of:
(e) determining whether the tachycardia has been converted to normal sinus rhythm.

6. The method of claim 5, further comprising repeating steps (a) through (e) if it is determined, at step (e), that the tachycardia has not been converted to normal sinus rhythm.

7. An implantable device for converting a ventricular tachycardia to normal sinus rhythm, comprising:

sensing circuit to sense a signal using a pair of electrodes adapted to be implanted in or adjacent a ventricle of a patient's heart;

an electrode switch adapted to short together the pair of electrodes; and controller to control delivery of anti-tachycardia pacing pulses to the ventricle using the shorted together pair of electrodes, wherein timing of at least one of the pacing pulses is based on the sensed signal.

8. The device of claim 7, wherein the pair of electrodes comprise a left ventricular (LV) tip electrode and an LV ring electrode adapted to be implanted in or adjacent the left ventricle of the heart.

9. The device of claim 7, wherein the pair of electrodes comprise a right ventricular (RV) tip electrode and an RV ring electrode adapted to be implanted in the right ventricle of the heart.

10. The device of claim 7, wherein the electrode switch is adapted to un-short the pair of electrodes following delivery of the anti-tachycardia pacing pulses.

11. The device of claim 10, further comprising:

means for determining whether the tachycardia has been converted to normal sinus rhythm.

12. A method for anti-tachycardia pacing, comprising the steps of:

(a) producing a sensed signal based on a right ventricular (RV) tip electrode and a RV ring electrode, both of which are implanted in the right ventricle;

(b) shorting together the RV tip electrode, the RV ring electrode, and an RV coil electrode, the RV coil electrode also implanted in the right ventricle; and (c) delivering anti-tachycardia pacing pulses to the right ventricle using the shorted together electrodes, wherein timing of at least one of the pacing pulses is based on the sensed signal.

13. An implantable device for converting a ventricular tachycardia to normal sinus rhythm, comprising:

a sensing circuit to sense a signal from a right ventricular (RV) tip electrode and a RV ring electrode, both of which are implanted in the right ventricle;

an electrode switch adapted to short together the RV tip electrode, the RV ring electrode, and an RV coil electrode, the RV coil electrode also inplanted in the right ventricle; and means for delivering anti-tachycardia pacing pulses to the right ventricle using the shorted together electrodes, wherein timing of at least one of the pacing pulses is based on the sensed signal.

* * * * *